United States Patent [19]
Baran et al.

[11] Patent Number: 4,657,931
[45] Date of Patent: Apr. 14, 1987

[54] N-(ACYLDIPEPTIDYL)-AMINOGLYCOLS
[75] Inventors: John S. Baran, Winnetka; Gunnar J. Hanson, Skokie, both of Ill.
[73] Assignee: G. D. Searle & Co., Skokie, Ill.
[21] Appl. No.: 734,296
[22] Filed: May 15, 1985
[51] Int. Cl.⁴ .................. A61K 31/16; C07K 7/02; C07C 103/20
[52] U.S. Cl. .................. 514/616; 564/158; 530/331; 530/332
[58] Field of Search ............ 260/112.5 R; 564/158; 530/331, 332; 514/616

[56] References Cited
PUBLICATIONS
Hanson, et al., Biochem—and Biophys. Res. Commun., pp. 155–161 (1985) vol. 132.

Primary Examiner—Delbert R. Phillips
Attorney, Agent, or Firm—Robert H. Benson; Mary Jo Kanady

[57] ABSTRACT

A compound of the formula:

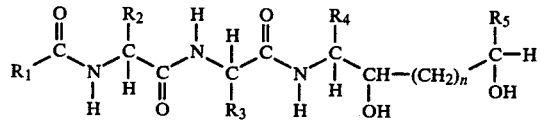

wherein $R_1$ is alkoxy containing one to six carbon atoms or lower alkyl containing one to six carbon atoms; $R_2$ is benzyl or napthylmethyl, $R_3$ is lower alkyl containing one to six carbon atoms or imidazolemethyl; $R_4$ is benzyl, $R_5$ is hydrogen or lower alkyl and n is 0 or 1. These compounds are useful as renin inhibitors.

11 Claims, No Drawings

N-(ACYLDIPEPTIDYL)-AMINOGLYCOLS

BACKGROUND OF THE INVENTION

1. Field of the Invention

The present invention describes novel N-(acyldipeptidyl)-aminoglycols which inhibit human renin.

The present invention is also concerned with pharmaceutical compositions containing the novel glycols of the present invention as active ingredients, and with diagnostic methods which utilize the novel glycols of the present invention.

Renin is a proteolytic enzyme of molecular weight about 40,000, produced and secreted by the kidney. It is secreted by the juxtaglomerular cells and acts on the plasma substrate, angiotensinogen, to split off the decapeptide angiotensin I, which is converted to the potent pressor agent angiotensin II. Thus, the renin-angiotensin system plays an important role in normal cardiovascular homeostasis and in some forms of hypertension.

In the past, attempts to modulate or manipulate the renin-angiotensin system have met with success in the use of inhibitors of angiotensin I converting enzyme. In view of this success, it is reasonable to conclude that a specific inhibitor of the limiting enzymatic step that ultimately regulates angiotensin II production, the action of renin on its substrate, would be at least equally successful. Thus, an effective inhibitor of renin has been long sought as a therapeutic agent, as an investigative tool, and as a diagnostic agent.

2. Description of the Prior Art

There has been a substantial interest in the synthesis of useful renin inhibitors for many decades; the following are the major classes of compounds which inhibit renin in vitro: renin antibodies, pepstatin and its analogs, phospholipids, analogs of angiotensinogen, pro-renin related analogs, and peptide aldehydes.

Umezawa et al., in *J. Antiobiot.* (Tokyo) 23: 259–262, 1970, reported the isolation of a peptide from actinomyces that was an inhibitor of aspartyl proteases such as pepsin, cathepsin D, and renin. This peptide, known as pepstatin, was found by Gross et al., *Science* 175: 656, 1971, to reduce blood pressure in vivo after the injection of hog renin into nephrectomized rats. However, pepstatin has not found wide application as an experimental agent because of its limited solubility and its inhibition of a variety of other acid proteases in addition to renin. Thus, investigators have synthesized modified pepstatins in an attempt to increase the specificity for human renin versus other physiologically important enzymes. Unfortunately, while some degree of specificity has been achieved, this approach has led to rather high molecular weight hepta- and octapeptides [Boger, et al., Nature 303, 81 (1983)]; high molecular weight peptides are generally considered undesirable as drugs because gastrointestinal absorption is impaired and plasma stability is compromised. The present invention relates to the use of low molecular weight dipeptide glycols.

Recently, Kokubu et al. *BBRC,* 118, 929 (1984), and Castro et al., *FEBS LETT.,* 167, 273 (1984) reported that short peptide aldehydes are renin inhibitors. While the molecular weight of the described compounds are indeed substantially lower than those described by Boger, these compounds, possessing a reactive C-terminal aldehyde group, are expected to be unstable in vivo, and thus their usefulness as therapeutic agents is compromised. The glycols of the present invention are of comparable molecular weight but contain no such therapeutically detrimental moiety as an aldehyde group; the active core is a physiologically compatible 1,2 diol group such as that found in the natural product glycerine.

European Patent Application 128762A discloses dipeptide and tripeptide renin inhibitors containing glycols, however, the aminoglycols of the present invention are chemically distinct from those disclosed in this application.

For other articles describing previous efforts to devise renin inhibitors, see Marshall, *Federation Proc.* 35: 2494–2501, 1976; Burton et al., *Proc. Natl. Acad. Sci. USA* 77: 5476–5479, Sept. 1980; Suketa et al., *Biochemistry* 14: 3188, 1975; Swales, *Pharmac. Ther.* 7: 173–201, 1979; Kokubu et al., *Nature* 217: 456–457, Feb. 3, 1968; Matsushita et al., *J. Antiobiotics* 28: 1016–1018, December 1975; Lazar et al., *Biochem. Pharma:* 23: 2776–2778, 1974; Miller et al., *Biochem. Pharma.* 21: 2941–2944 1972; Haber, *Clinical Science* 59: 7s–19s, 1980; Rich et al., *J. Org. Chem.* 43: 3624, 1978, *J. Med. Chem.* 23: 27, 1980; and especially Haber, *Clin. and Exper. Hyper.,* A5(7&8), 1193 (1983).

SUMMARY OF THE INVENTION

A compound of the formula:

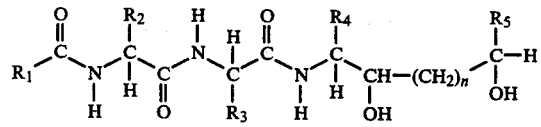

wherein $R_1$ is alkoxy containing one to six carbon atoms or lower alkyl containing one to six carbon atoms; $R_2$ is benzyl or napthylmethyl, $R_3$ is lower alkyl containing one to six carbon atoms or imidazolemethyl; $R_4$ is benzyl, $R_5$ is hydrogen or lower alkyl containing 1 to 6 carbon atoms and n is 0 or 1.

DETAILED DESCRIPTION OF THE INVENTION

A compound of the formula:

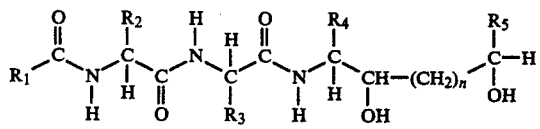

wherein $R_1$ is alkoxy containing one to six carbon atoms or lower alkyl containing one to six carbon atoms; $R_2$ is benzyl or napthylmethyl, $R_3$ is lower alkyl containing one to six carbon atoms or imidazolemethyl; $R_4$ is benzyl, $R_5$ is hydrogen or lower alkyl containing 1 to 6 carbon atoms and n is 0 or 1.

$R_1$ is straight or branched chain alkoxy of one to six carbons, or straight or branched chain alkyl of one to six carbons. Straight or branched lower alkyl groups may be selected from the group methyl, ethyl, propyl, isopropyl, butyl, isobutyl, tert-butyl, pentyl and the like, hexyl and the like. Alkoxy contains a lower alkyl. $R_2$ is benzyl or napthylmethyl. $R_3$ is straight or branched alkyl containing one to six carbon atoms as described or imidazolemethyl. $R_4$ is benzyl. $R_5$ is hydrogen or lower alkyl containing one to six carbon atoms. "n" or 0 or 1. The compounds of this invention may have R or S stereo chemistry at the asymmetric centers. However, S.S.S.R. stereochemistry from left to right are preferred when n=0, S.S.S.S. is preferred when n=1.
Synthetic Scheme 1 describes the synthesis of the compounds of this invention when n is 0. Synthetic Scheme 2 describes the synthesis of the compounds of this invention when n is 1.
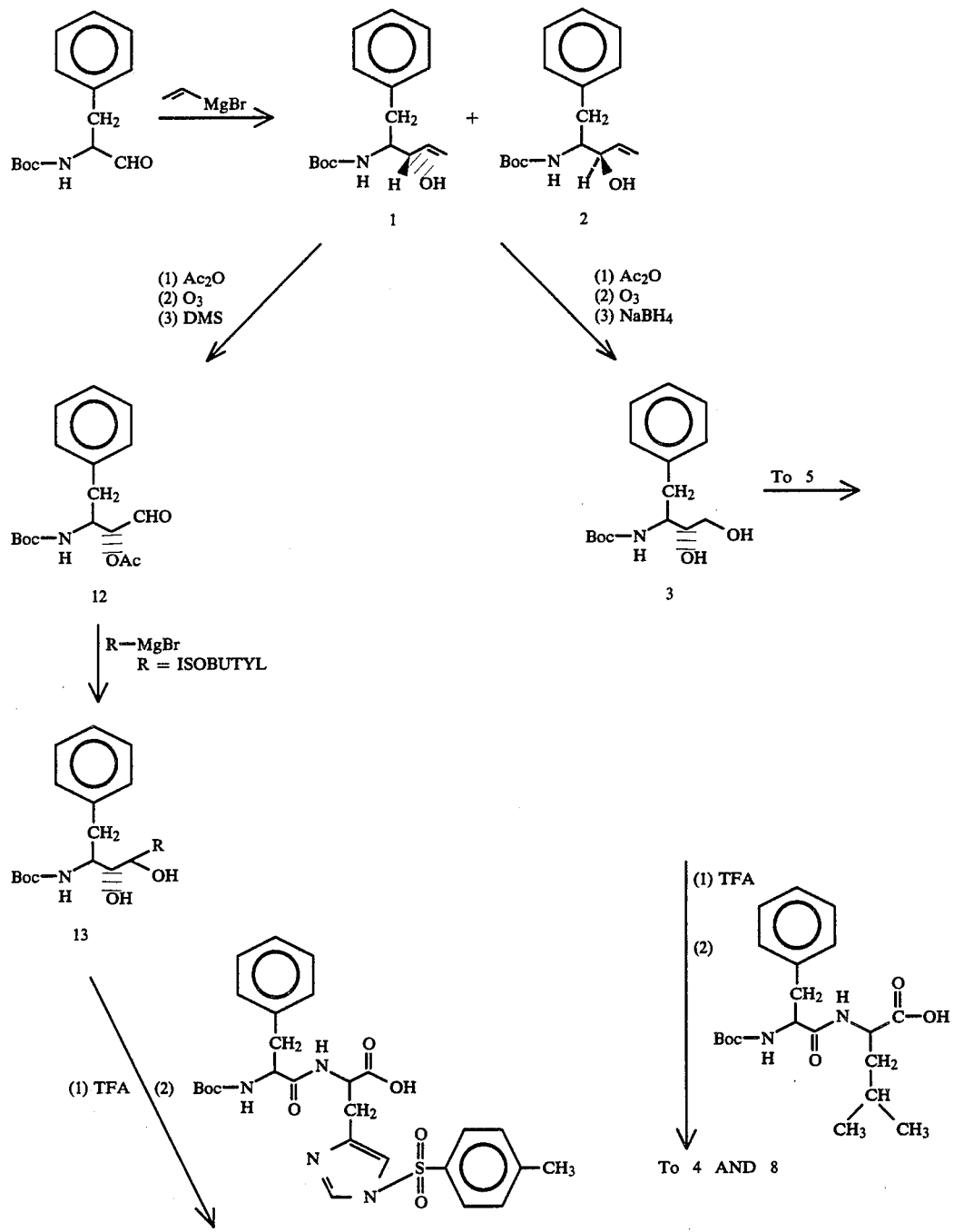

4,657,931
-continued
SCHEME 1
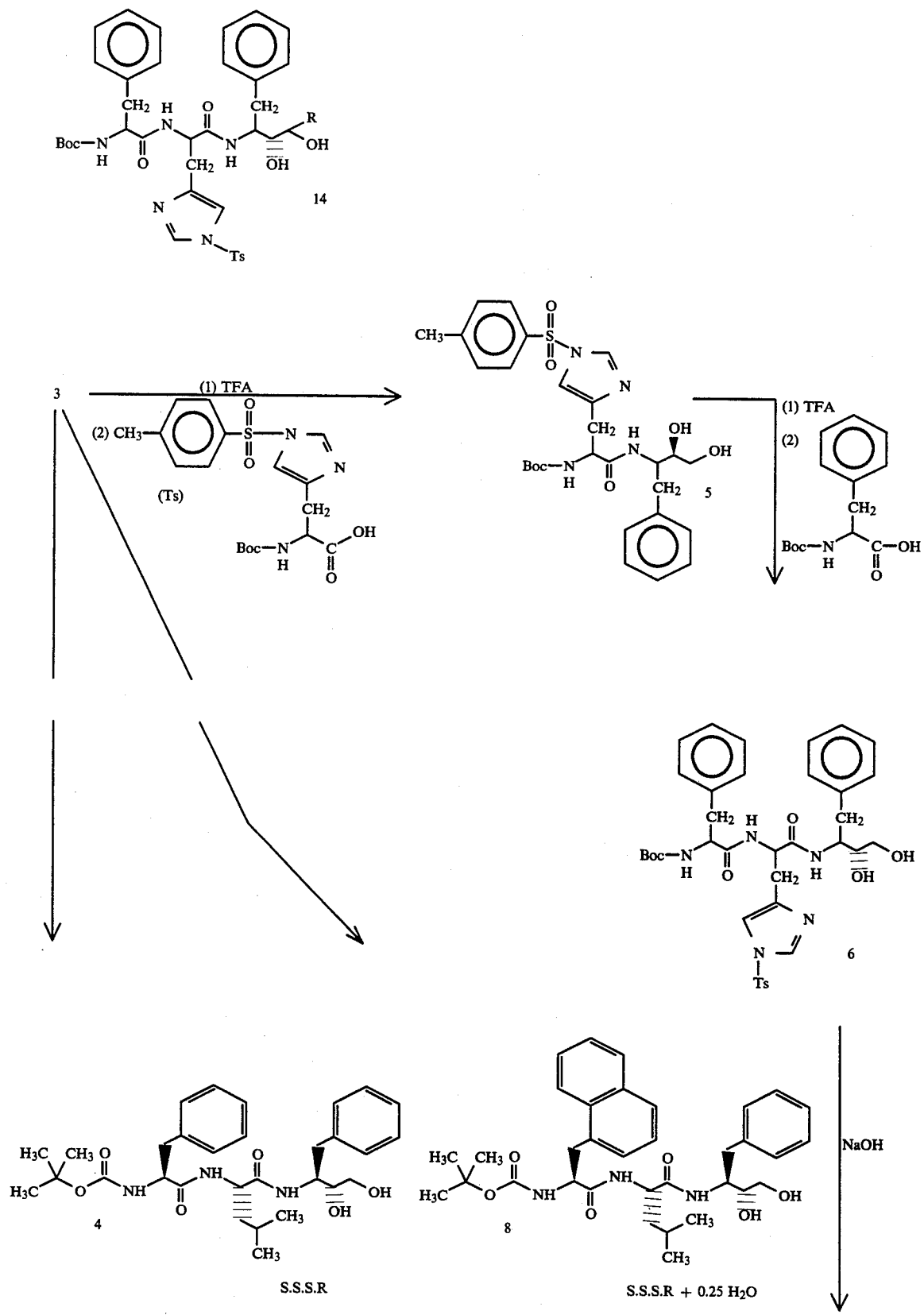

-continued
SCHEME 1

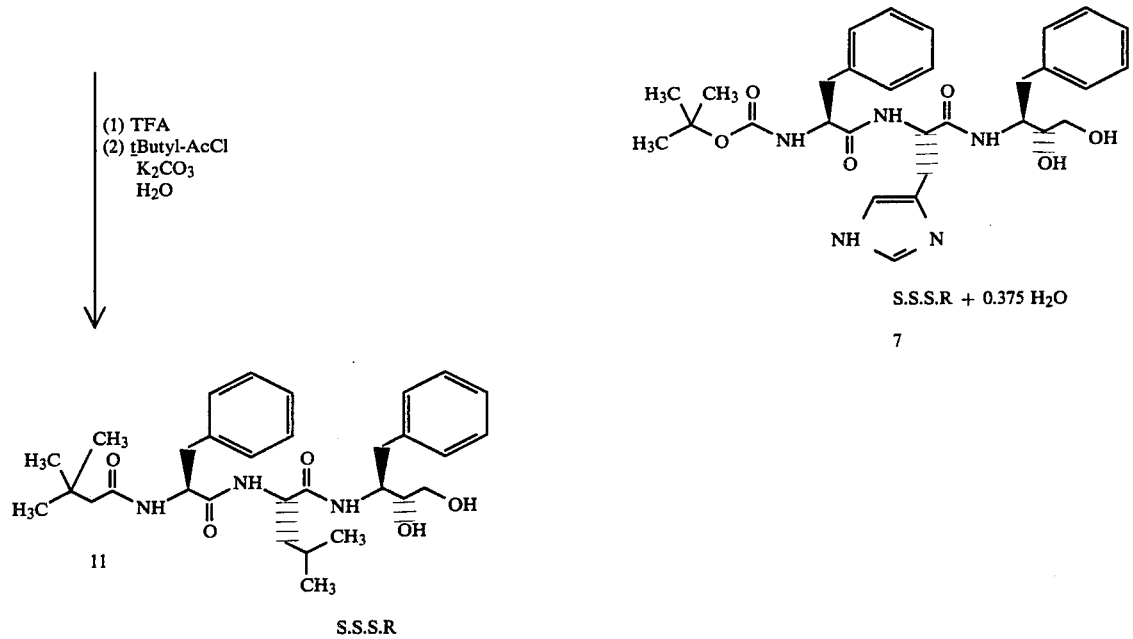

S.S.S.R + 0.375 H₂O

7

SCHEME 2

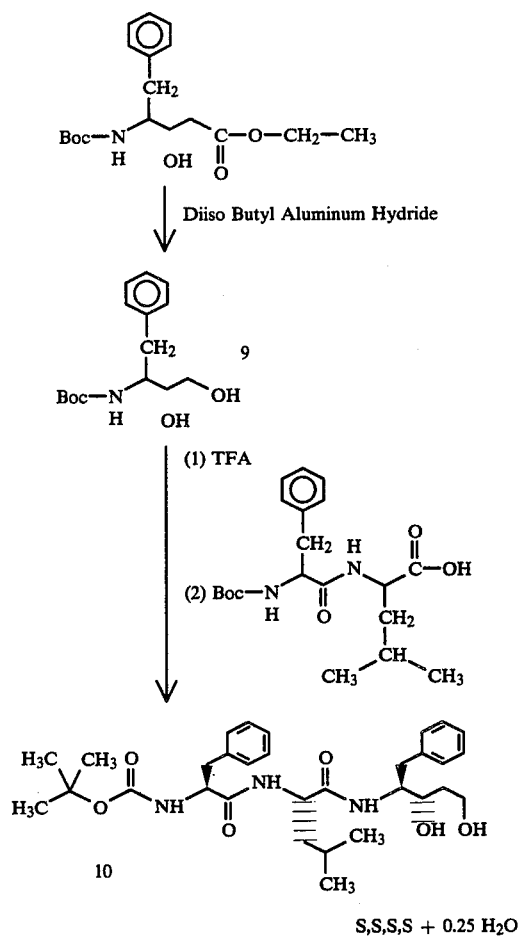

S,S,S,S + 0.25 H₂O

DESCRIPTION OF THE PROCESS DEPICTED IN SCHEME 1 WHEN (n=0)

Preparation of 1,2 Diol Renin Inhibitors (Scheme 1)

A suitably protected α-amino aldehyde, for example Boc-phenylalaninal, was treated with vinylmagnesium bromide to give, after standard workup, a mixture of diastereomeric allylic alcohols compound 1 and compound 2 which were separated using HPLC. Since compound 1 possesses the correct stereochemistry at C-3 for biological activity, it was further elaborated in two ways. In one route, compound 1 was acetylated with acetic anhydride-pyridine to produce an acetate which was then subjected to ozone at −78° in methanol, followed by sodium borohydride workup and sodium hydroxide hydrolysis to give key intermediate diol compound 3. This compound was then deblocked using trifluoroacetic acid at room temperature for 30 min; the resulting salt was coupled to various N-protected dipeptide acids using standard mixed carbonic anhydride methodology to give renin inhibitors compound 4 and compound 8. Compound 4 was treated with trifluoroacetic acid followed by tert-butylacetyl chloride-potassium carbonate in water-ethyl acetate to give renin inhibitor compound 11. Compound 3 was deblocked with trifluoroacetic acid and coupled to a Boc-protected amino acid, for example, Boc-L-His(Ts)-OH, using standard procedures to give compound 5; this material was then deblocked and coupled to a Boc-protected amino acid, for example, Boc-L-Phe-OH, to give compound 6 which was converted to renin inhibitor compound 7 upon treatment with sodium hydroxide in water-tetrahydrofuran. In another route, allylic alcohol compound 1 is acetylated and ozonized as described above, except this time a dimethyl sulfide workup is employed which produces acetoxy-aldehyde compound 12. This compound is treated with various organometallic reagents, such as isobutylmagnesium chloride, to give diols such as compound 13; these diols are then deblocked and coupled in the usual manner with N-protected dipeptide acids to give renin inhibitors of the type of compound 14.

DESCRIPTION OF THE PROCESS DEPICTED IN SCHEME 2

(n=1)

Preparation of 1,3 Diol Renin Inhibitors

A Boc-protected (S,S) statine ester derivative, for example (3S,4S)-N-tert-butyloxycarbonyl-4-amino-3-hydroxy-5-phenylpentanoic acid ethyl ester, was reduced with diisobutylaluminum hydride to give 1,3 propanediol compound 9 which was deblocked and coupled in the usual manner with a Boc-protected dipeptide acid to give renin inhibitor compound 10. Boc is t-butyloxycarbinyl.

The amino group at the N-terminus can be reacted with succinic arhydride to form a hemisuccinamide. Also, succinic anhydride be reacted with one or both alcohols at the glycol end to form succinic esters.

Any inhibitor of renin inhibits the production of angiotensis II production and thus acts as a therapeutic agent. Angiotensin II is a potent vasoconstrictor and participates in aldosterone formation, and thus is intimately involved in the regulation of blood pressure and sodium retention.

By virtue of this activity, the compounds of this invention are useful in treating high blood pressure in mammals. A physician or veterinarian of ordinary skill can readily determine whether a subject exhibits hypertension. Regardless of the route of administration selected, the compounds of the present invention are formulated into pharmaceutically acceptable dosage forms by conventional methods known to those skilled in the art. The compounds may be formulated using pharmacologically acceptable acid addition salts. Moreover, the compounds or their salts may be used in a suitable hydrated form.

The compounds can be administered in such oral dosage forms as tablets, capsules, pills, powders, or granules. They may also be administered intravascularly, intraperitoneally, subcutaneously, or intramuscularly, using forms known to the pharmaceutical art. In general, the preferred form of administration is oral. An effective but non-toxic quantity of the compound is employed in treatment. The dosage regimen for preventing or treating hypertension with the compounds of this invention is selected in accordance with a variety of factors, including the type, age, weight, sex, and medical condition of the patient; the severity of the hypertension; the route of administration; and the particular compound employed. An ordinarily skilled physician or veterinarian can readily determine and prescribe the effective amount of the drug required to prevent or arrest the progress of the condition. In so proceeding, the physician or veterinarian could employ relatively low doses at first and subsequently increase the dose until a maximum response is obtained. Dosages of the compounds of the invention are ordinarily in the range of 1.0 to 20 mg/kg up to about 200 mg/kg orally or by injection.

The following examples further illustrate details for the preparation of the compounds of this invention. The invention, which is set forth in the foregoing disclosure, is not to be construed or limited either in spirit or in scope by these examples. Those skilled in the art will readily understand that known variations of the conditions and processes of the following preparative procedures can be used to prepare these compounds.

EXAMPLE 1

Synthesis Compounds 1 and 2

N-(tert-Butyloxycarboxyl)-4(S)-amino-3(S)-hydroxy-5-phenylpentene (1) and N-(tert-Butyloxycarbonyl-4(S)-amino-3(R)-hydroxy-5-phenylpentene (compound 2)

To a cooled (−78°) solution of Boc-L-phenylalaninal (16.77 g, 67 mmol) in tetrahydrofuran (100 mL) was added dropwise vinylmagnesium bromide (201 mL, 1M in tetrahydrofuran). After the addition was complete, the reaction mixture was allowed to warm to room temperature. It was then poured into saturated aqueous ammonium chloride, and extracted with several portions of ether. The combined organic extracts were dried over MgSO$_4$, and evaporated under aspirator vacuum to give crude allylic alcohol (Compound 1, Scheme 1) admixed with its epimer (Compound 2, Scheme 1) (19.6 g crude product). The crude product (5 g) was purified by HPLC on silica gel, eluting with 20% ethyl acetate in toluene to give, after recrystallization from ethyl acetate-hexanes, pure Compound 1:

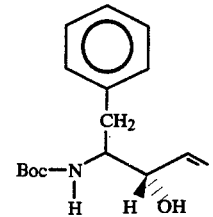

(800 mg): mp 101.8°–102.8°; $[\alpha]_D^{25}$ −53.2° (C=1, CHCl$_3$);

$^1$H NMR: 200 MHz spectrum consistent with proposed structure.

Anal. Calcd. for C$_{16}$H$_{23}$NO$_3$: C, 69.28; H, 8.35; N, 5.04. Found: C, 69.29; H, 8.15; N, 5.01.

Pure epimer (Compound 2, 1 g) was also isolated: mp 125°–126.5°; $[\alpha]_D^{25}$ −23.6° (C=1, CHCl$_3$); $^1$H NMR: 200 MHz spectrum consistent with proposed structure.

Anal. Found: C, 69.39; H, 8.06; N, 5.05.

Synthesis Compound 3

N-(tert-Butyloxycarbonyl)-3(S)-amino-2(R)-hydroxy-4-phenylbutanol

The allylic alcohol (Compound 1, 1 g, 3.6 mmol) was dissolved in acetic anhydride (10 mL) and pyridine (5 drops) was added. This solution was allowed to stand overnight, then poured into a slurry of sodium bicarbonate (20 g) and water (75 mL). After gas evolution ceased, the acetate of compound 1 was extracted with several portions of ether. The organic layers were combined, dried over Na$_2$SO$_4$, and the solvent was evaporated at reduced pressure to give crystalline acetate (1.1 g, 96% yield) mp 58°–61°. This was dissolved in methanol (20 mL) and cooled to −78°. Ozone was then bubbled in until a blue color persisted; the excess ozone was purged with oxygen and sodium borohydride (240 mg) in methanol (1 mL) was added. The mixture was allowed to warm to room temperature and stir for 0.5 h.

Sodium hydroxide (300 mg) in water (5 ml) was added, and the mixture was stirred for an additional 1 h at R.T. Citric acid (0.5M was added until a pH of 7 was obtained. The solution was then evaporated and the residue extracted with ethyl acetate. The organic solution was then washed with citric acid (0.5M), sodium bicarbonate (5%), brine, and then evaporated to obtain compound 3 as an oil. This was crystallized from ethyl acetate-hexanes to give compound 3 as colorless crystals (820 mg, 82% yield):

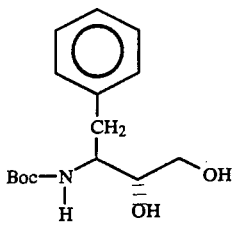

mp 88.5–90.50; $[\alpha]_D^{25}$ −36.8° (C=1, CHCl$_3$);

$^1$H NMR: 200 MHz spectrum consistent with proposed structure.

Anal. Calcd. for $C_{15}H_{23}NO_4$: C, 64.03; H, 8.23; N, 4.97. Found: C, 64.02; H, 8.31; N, 4.86.

The diacetate of compound 3 was prepared by reaction with acetic anhydride/pyridine and resulted in a compound with the following properties: mp 94°–96°; $^1$H NMR (CDCl$_2$)δ: 2.01 (S, 3H, CH$_3$CO—), 2.09(S, 3H, CH$_3$CO—), 5.0–5.2(m, 1H, CHOAc).

Anal. Calcd. for $C_{19}H_{27}NO_6$: C, 62.45; H, 7.44; N, 3.83. Found: C, 62.22; H, 7.29; N, 3.74.

Synthesis Compound 4

N-[(1,1-dimethylethoxy)carbonyl]-L-phenylalanyl-N-[2R, 3-dihydroxy-1S-(phenylmethyl)propyl]-L-leucinamide Compound 3 (255 mg, 0.91 mmole) was dissolved in trifluoroacetic acid-water (9:1, 5 mL) at room temperature and allowed to stand for 30 min. The solvent was evaporated; this amine trifluoroacetate was then coupled to Boc-L-Phe-L-Leu-OH according to the method of Benoiton in *J. Org. Chem.* 48, 2939(1983), as follows:

Boc-L-Phe-L-Leu-OH(0.5 g, 1.3 mmol) was mixed with methylene chloride (5 mL) and N-methyl piperidine (130 mg, 1.3 mmol) and cooled to −10°. Isobutylchloroformate (170 mg, 1.25 mmol) was added; after 3.5 min. of stirring at −10°, a solution of the above amine trifluoroacetate and N-methyl piperidine (99 mg, 0.9 mmol) was added. The solution was allowed to warm to 0° over a 0.5 h. period and was kept at 0° for 8 h. The reaction mixture was then evaporated and the residue partitioned between ethyl acetate and water. The organic phase was washed successively with citric acid (0.5M), sodium bicarbonate (5%), and brine. The solution was dried over sodium sulfate and evaporated to give compound 4 as an oil, which was taken up in methanol-methylene chloride (1:9, 5 m L) and filtered through a short pad of silica. The filtrate was evaporated and triturated with ether; the solid was collected on a filter plate to give pure compound 4 (138 mg, 28% yield) as a crystalline solid:

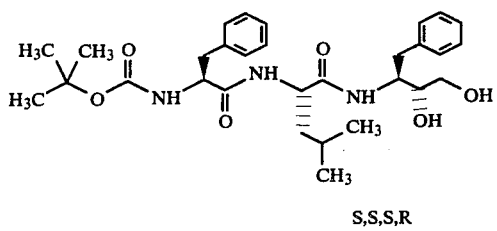

S,S,S,R mp 174°–176°; $[\alpha]_D^{25}$ −62.4° (C=1.02, CHCl$_3$);

$^1$H NMR: 200 MHz spectrum consistent with proposed structure; HPLC: greater than 99% single peak; TLC: silica, methylene chloride-methanol (9:1) single spot (I$_2$ positive).

Anal. Calcd. for $C_{30}H_{43}N_3O_6$: C, 66.53; H, 7.97; N, 7.75. Found: C, 66.28; H, 8.01; N, 7.73.

EXAMPLE 2

Synthesis Compound 5

N-(tert-Butyloxycarbonyl)-im-tosyl-L-histidyl-3(S)-amino-2(R)-hydroxy-4-phenylbutanol amide N-(tert-Butyloxycarbonyl)-im-tosyl-L-histidine (1.19 g, 2.9 mmol) was coupled to compound 3 (0.5 g, 1.7 mmol) in the manner described above for the synthesis of compound 4. The reaction was terminated after 4 h; the solvent was evaporated and the residue partitioned between water and ethyl acetate. The organic layer was washed with citric acid (0.5M), sodium bicarbonate (5%), and brine. The solvent was evaporated, the glassy residue was triturated with methylene chloride, and compound 5, as a white crystalline solid, was collected on a filter plate (650 mg, 65% yield). The amide was recrystallized from methanol-ether to give pure compound 5 (550 mg):

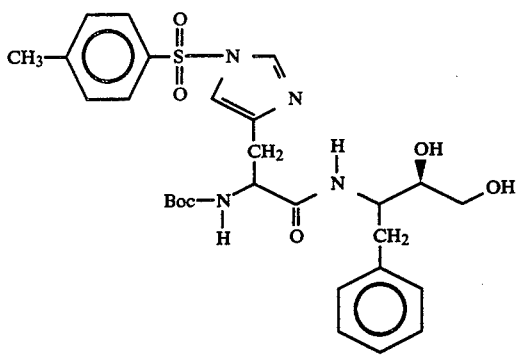

mp 183°–186°, $^1$H NMR: 80 MHz spectrum consistent with proposed structure; TLC: silica, methanol-methylene chloride (1:9), single spot.

Anal. Calcd. for $C_{28}H_{36}N_4O_7S$: C, 58.72; H, 6.33; N, 9.77. Found: C, 58.47; H, 6.26; N, 9.69.

Synthesis Compound 6

N-(tert-Butyloxycarbonyl)-L-phenylalanyl-im-tosyl-L-histidyl-3(S)-amino-2(R)-hydroxy-4-phenylbutanol amide Compound 5 (300 mg, 0.52 mmol) was dissolved in trifluoroacetic acid-methanol (9:1, 10 mL) and allowed to stand at room temperature for ½ h. The solvent was evaporated under aspirator pressure, and the residue triturated with ether-hexanes (1:1). The resulting white solid was collected on a filter plate (280 mg, 91% yield), and without further purification was coupled (200 mg, 0.34 mmol) to N-(tert-Butyloxycarbonyl)-L-phenylalanine (0.2 g, 0.75 mmol) according to the procedure described for compound 4. The reaction mixture was evaporated, partitioned between ethyl acetate and water, and the organic layer was washed with citric acid, sodium bicarbonate (5%), and brine. After drying over Na₂SO₄ and evaporation, a solid remained; this was triturated with methylene chloride-ether (1:1) to give an off-white solid. This was dissolved in methylene chloride-methanol (9:1) was filtered through a short pad of silica gel. The filtrate was evaporated to give compound 6 as a tan solid (118 mg, 48% yield):

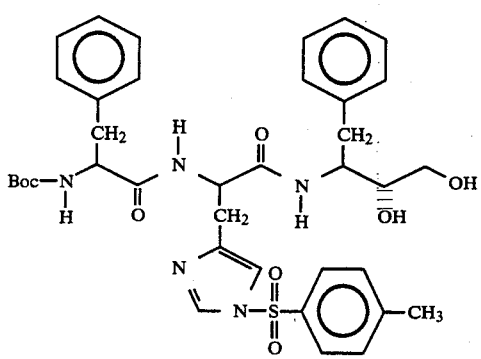

mp 166.5°-169° (dec.);
TLC: silica, methylene chloride-methanol (9:1), single spot (iodine and UV visualization).
Anal. Calcd. for $C_{37}H_{45}H_5O_8S.\frac{1}{2}H_2O$: C, 60.97; H, 6.35; N, 9.60. Found: C, 60.77; H, 6.16; N, 9.42.

Synthesis Compound 7

N-[(1,1-dimethylethoxy)carbonyl]-L-phenylalanyl-N-[2R,3-dihydroxy-1S-(phenylmethyl)propyl]-L-histidinamide Compound 6 (118 mg, 0.16 mmol) was mixed with tetrahydrofuran (3 mL) and a solution of sodium hydroxide (50 mg) in water (0.5 mL) was added. This mixture was stirred at 20° for 45 min., then the solvent evaporated to give a white solid. This solid was dissolved in citric acid (0.5M), the aqueous solution washed with ethyl actate, then basified to pH8 with potassium carbonate (5%). The resulting precipitate was collected on a filter plate and washed with ethyl acetate to give pure compound 7:

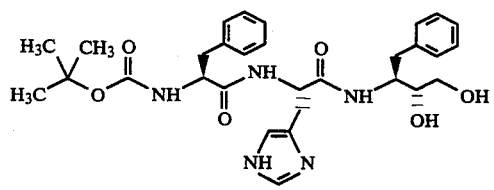

S,S,S,R + 0.375 H₂O mp 200.5°-202° C.;
TLC: silica, 30% methanol in methylene chloride, single spot (iodine).

¹H NMR: 200 MHZ spectrum consistent with the proposed structure.
Anal. Calcd. for $C_{30}H_{39}N_5O_6.\frac{3}{8}H_2O$: C, 62.94; H, 6.99; N, 12.22. Found: C, 63.00; H, 6.79; N, 12.11.

EXAMPLE 3

Synthesis Compound 8

N-[(1,1-dimethylethoxy)carbonyl]-3-(1-naphthalenyl)-L-alanyl-N-[2R,3-dihydroxy-1S-(phenylmethyl)-propyl]-L-leucinamide N-(tert-Butyloxycarbonyl)-[3-1'-napthyl)-L-alanyl]-L-leucine (300 mg, 0.7 mmol) was coupled to compound 3 in the manner described above for the synthesis of compound 4. Compound 8 was obtained as a white solid (130 mg, 31% yield): mp 172°-176.6°; TLC: silica, methylene chloride-methanol (9:1), single spot (UV and iodine visualization).

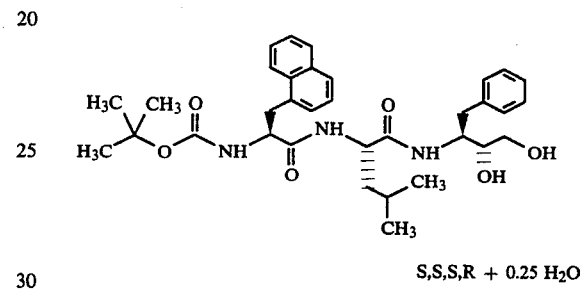

S,S,S,R + 0.25 H₂O

Anal. Calcd. for $C_{34}H_{45}N_3O_6.\frac{1}{4}H_2O$: C, 68.49; H, 7.69; N, 7.04. Found: C, 68.35; H, 7.57; N, 6.99.

EXAMPLE 4

Synthesis Compound 9

N-(tert-Butyloxycarbonyl)-4(S)-amino-3(S)-hydroxy-5-phenylpentanol

N-(tert-Butyloxycarbonyl-4(S)-amino-3(S)-hydroxy-5-phenylpentanoic acid ethyl ester (2 g, 5.9 mmol), prepared as described by Rich, in *Journal of Medicinal Chemistry* 23, 27 (1980), was dissolved in ether (30 mL), cooled to 0° and treated with diisobutylaluminum hydride (40 mL, 1M in hexanes). This mixture was stirred at 0° for 1 h., then water was added followed by saturated Rochelle salt. When the phases separated, the mixture was extracted with ethyl acetate. The organic layer was washed with water and evaporated to give a pink oil, which crystallized upon addition of etherphexanes (1:1). These crystals were taken up in methylene chloride (9:1) and the solution passed through a pad of silica gel. The filtrate was evaporated and recrystallized from ethyl acetate-hexanes to give pure compound 9 (500 mg, 29% yield): mp 107.2°-108.5°;
¹H NMR 80 MHz spectrum consistent with the following structure:

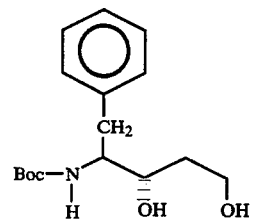

Anal. Calcd. for $C_{16}H_{25}NO_4 \cdot 1/8H_2O$: C, 64.57; H, 8.54; N, 4.70. Found: C, 64.60; H, 8.34; N, 4.83.

Synthesis Compound 10

N-[(1,1-dimethylethoxy)carbonyl]-L-phenylalanyl-N-[2S,4-dihydroxy-1S-(phenylmethyl)butyl]-L-leucinamide N-(tert-Butyloxycarbonyl)-L-phenylalanyl-L-leucine (500 mg, 1.3 mmol) was coupled to compound 9 (200 mg, 0.68 mmol) in the manner described for the preparation of compound 4. A tan powder was obtained as the crude product; this was chromatographed on silica, elutting with methylene chloride-methanol (9:1) to give pure compound 10 (102 mg, 27% yield):

$^1$H NMR: 200 MHz spectrum consistent with the following structure:

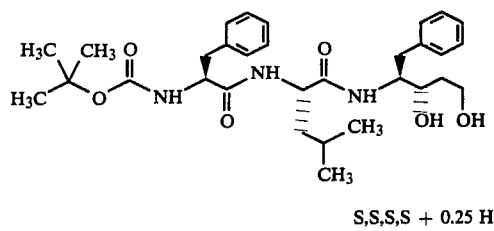

S,S,S,S + 0.25 $H_2O$

Anal. Calcd. for $C_{31}H_{45}N_3O_6 \cdot \frac{1}{4}H_2O$: C, 66.56; H, 8.18; N, 7.49. Found: C, 66.41; H, 8.00; N, 7.57.

EXAMPLE 5

Synthesis Compound 11

N-(3,3-dimethyl-1-oxobutyl)-L-phenylalanyl-N-[2R,3-dihydroxy-1S-(phenylmethyl)propyl]-L-leucinamide Compound 4 (200 mg, 0.38 mmol) was dissolved in trifluoroacetic acid-methanol (9:1, 5 mL) and the solution was allowed to stand at room temperature for 0.5 h. The solvent was evaporated at reduced pressure and the residue dissolved in water (5 mL). To this was added solid potassium carbonate (10 mg) along with ethyl acetate (5 ml). The tert-butylacetyl chloride (66 mg, 0.49 mmol) was added and the biphasic mixture was stirred at room temperature for 30 min. The organic layer was separated, washed with sodium bicarbonate (5%), water, and brine. The solvent was evaporated to obtain, after trituration with hexanes, a white solid. This was recrystallized from methanol in ethyl acetate (5%) to give pure compound 11 (150 mg, 75% yield) as fine needles with the following structure: mp 183°–185°.

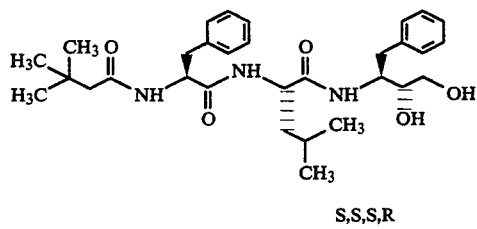

S,S,S,R

Anal. Calcd. for $C_{31}H_{45}O_5N_3$: C, 68.99; H, 8.40; N, 7.79. Found: C, 68.93; H, 8.55; N, 7.80.

EXAMPLE 6

Biological Activity of N-(acyldipeptidyl)-aminoglycols

The aminoglycols of the invention were evaluated for their ability to inhibit human renin in vitro and monkey renin in vivo. The results of these tests are in Table 1 and Table 2.

Human Renin Test

The enzyme preparation was the international reference standard for human renin while human blood plasma was the angiotensinogen substrate source. The enzyme inhibition assay involved a two-hour incurbation at 37° C. of the following final concentrations of reagents (total volume of 0.25 ml): 0.1 mG units/ml human renin, 0.05 ml human plasma, 6 mM $Na_2EDTA$, 2.4 mM PMSF, 1.5 mM 8-hydroxyquinoline, 0.4 mg/ml BSA, 0.024 mg/ml neomycin sulfate in a 100 mM Tris Acetate buffer, pH 7.5. The reaction was terminated by boiling for 10 min and the angiotensin I produced was determined by radioimmunoassay. Compounds that inhibit renin activity by 20% or more at the initial screening concentration are considered active.

This assay is a modification of the one by Burton et al. (*Biochemistry* 14, 3892, 1975). The reference standard used were pro[phe$^6$] octapeptide and pepstatin with $IC_{50}$ values of $6 \times 10^{-6}$M and $1.4 \times 10^{-5}$M respectively.

TABLE 1

| Effect of Compounds on Human Renin Activity | | |
|---|---|---|
| Compound | Dose | Activity |
| Compound 4 | $8.4 \times 10^{-6}$ | Active |
| Compound 8 | $1.5 \times 10^{-5}$ | Active |
| Compound 7 | $2.6 \times 10^{-6}$ | Active |
| Compound 11 | $4 \times 10^{-6}$ | Active |

Monkey Renin Test

Rhesus monkeys (6/group) weighing (6.3–9.9 kg) were treated with lasix (furosemide) at 2 mg/kg, both in the A.M. and P.M. on day 1. On day 2, compound 4 at 10 mg/kg, iv or pepstatin at 10 mg/kg, iv was administered. Plasma samples (K-EDTA) were taken before the initial lasix, immediately before the drug treatment and at 2, 5, 15 min after the treatment. Plasma renin activity (PRA) was determined by the method of Burton et al., *Biochemistry* 14, 3892, 1975.

Table 1 shows the PRA for both the pepstatin treated and the compound 4 group. For both groups, PRA is increased by lasix and is returned to pre-lasix values at 2 min after treatment. The compound 4 treated group's PRA is still lowered after 15 min while the pepstatin group has returned to post-lasix levels.

TABLE 2

| The Effect of Compound 4 and Pepstatin on Plasma Renin Activity of Lasix Treated Rhesus Monkeys | | |
|---|---|---|
| Time | Pepstatin (n = 6) | Compound 4 (n = 6) |
| Pre-Lasix −24 hr | 13.9 ± 2.5$^a$ | 12.2 ± 2.9 |
| Post-Lasix | | |
| 0 hr | 53.1 ± 6.1 | 47.2 ± 7.9 |
| 2 min | 13.0 ± 0.2 | 8.4 ± 2.6 |
| 5 min | 22.7 ± 9.2 | 15.1 ± 3.5 |
| 15 min | 44.7 ± 5.4 | 23.5 ± 4.6 |

$^a$mean ± S.E.

We claim:
1. A compound of the formula:

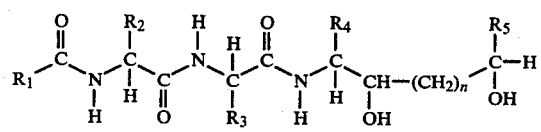

wherein $R_1$ is alkoxy containing one to six carbon atoms or alkyl containing one to six carbon atoms; $R_2$ is benzyl or napthylmethyl, $R_3$ is lower alkyl containing one to six carbon atoms or imidazolemethyl; $R_4$ is benzyl, $R_5$ is hydrogen or lower alkyl and n is 0 or 1.

2. A compound of chain 1 wherein $R_3$ is lower alkyl containing one to six carbons.

3. A compound of claim 1 wherein $R_3$ is imidazolemethyl.

4. A compound according to claim 2 comprising N-[(1,1-dimethylethoxy)carbonyl]-L-phenylalanyl-N-[2S,4-dihydroxy-1S-(phenylmethyl)butyl]-L-leucinamide.

5. A compound according to claim 2 comprising N-[(1,1-dimethylethoxy)carbonyl]-L-phenylalanyl-N-[(2R,3-dihydroxy-1S-(phenylmethyl)propyl]-L-leucinamide.

6. A compound according to claim 2 comprising N-[(1,1-dimethylethoxy)carbonyl]-3-(1-naphthalenyl)-L-alanyl-N-[2R,3-dihydroxy-1S-(phenylmethyl)propyl]-L-leucinamide.

7. A compound according to claim 3 comprising N-[(1,1-dimethylethoxy)carbonyl]-L-phenylalanyl-N-[2R,3-dihydroxy-1S-(phenylmethyl)propyl]-L-histidinamide.

8. A compound according to claim 2 comprising N-(3,3-dimethyl-1-oxobutyl)-L-phenylalanyl-N-[2R,3-dihydroxy-1S-(phenylmethyl)propyl]-L-leucinamide.

9. A renin-inhibiting composition of matter comprising a therapeutically effective amount of the compound of claim 1 suitable for pharmaceutical administration.

10. The composition of claim 9 suitable for oral administration.

11. The composition of claim 9 suitable for parenteral administration.

* * * * *